(12) United States Patent
Toreki et al.

(10) Patent No.: US 8,333,743 B2
(45) Date of Patent: Dec. 18, 2012

(54) ANTIMICROBIAL BANDAGE MATERIAL COMPRISING SUPERABSORBENT AND NON-SUPERABSORBENT LAYERS

(75) Inventors: William Toreki, Gainesville, FL (US); Gerald Olderman, Bedford, MA (US); Gregory Schultz, Gainesville, FL (US); Christopher Batich, Gainesville, FL (US)

(73) Assignees: Quick-Med Technologies, Inc., Gainesville, FL (US); University of Florida Research Foundation, Inc., Gainesville, FL (US)

( * ) Notice: Subject to any disclaimer, the term of this patent is extended or adjusted under 35 U.S.C. 154(b) by 57 days.

(21) Appl. No.: 12/772,686

(22) Filed: May 3, 2010

(65) Prior Publication Data

US 2010/0211035 A1    Aug. 19, 2010

Related U.S. Application Data

(63) Continuation of application No. 09/965,740, filed on Sep. 28, 2001, now Pat. No. 7,709,694, which is a continuation-in-part of application No. PCT/US99/29091, filed on Dec. 8, 1999.

(60) Provisional application No. 60/111,472, filed on Dec. 9, 1998.

(51) Int. Cl.
*A61F 13/00* (2006.01)
(52) U.S. Cl. .................... 604/304; 602/48; 427/2.31
(58) Field of Classification Search .......... 604/304–308; 602/48; 427/3.2–3.21, 2.3–2.31
See application file for complete search history.

(56) References Cited

U.S. PATENT DOCUMENTS

| 5,035,892 | A  |   | 7/1991 | Blank et al. |
| 5,648,400 | A  | * | 7/1997 | Sugo et al. ................... 521/30 |
| 5,783,502 | A  | * | 7/1998 | Swanson ....................... 442/123 |
| 6,200,354 | B1 | * | 3/2001 | Collins et al. ..................... 8/554 |
| 6,447,640 | B1 | * | 9/2002 | Watson et al. ................ 162/101 |
| 6,740,373 | B1 | * | 5/2004 | Swoboda et al. ............ 428/34.2 |

* cited by examiner

*Primary Examiner* — Lynne Anderson
(74) *Attorney, Agent, or Firm* — Gerry J. Elman; Elman Technology Law, P.C.

(57) ABSTRACT

This invention relates to methods and compositions for materials having a non-leaching coating that has antimicrobial properties. The coating is applied to substrates such as gauze-type wound dressings. Covalent, non-leaching, non-hydrolyzable bonds are formed between the substrate and the polymer molecules that form the coating. A high concentration of anti-microbial groups on multi-length polymer chains and relatively long average chain lengths, contribute to an absorbent or superabsorbent surface with a high level antimicrobial effect.

20 Claims, No Drawings

ANTIMICROBIAL BANDAGE MATERIAL COMPRISING SUPERABSORBENT AND NON-SUPERABSORBENT LAYERS

CROSS-REFERENCE TO RELATED APPLICATIONS

This application is a continuation of our U.S. application Ser. No. 09/965,740, filed Sep. 28, 2001 and scheduled to be issued May 4, 2010 as U.S. Pat. No. 7,709,694, which is a continuation in part of PCT application Ser. No. PCT/US99/29091, filed Dec. 8, 1999, now abandoned, which is a continuation of U.S. Provisional application Ser. No. 60/111,472, filed Dec. 8, 1998, to which the benefit of priority is claimed under 35 USC §§119 and 120. The entire disclosure of each of the above-named applications and/or patents is hereby incorporated by reference.

BACKGROUND OF THE INVENTION

The importance of sterile techniques and especially sterile bandage material to modern medicine can hardly be overestimated. Almost every student of biology has heard the tales of how medical practitioners of not too long ago thought that pus and other signs of what is now known to be infection were essential to wound healing. These practitioners would reopen a wound that was not showing the expected pus and inflammation. This was changed by Lister's discoveries regarding disinfection and the subsequent adoption of sterile bandage material for wound dressings. A continuing problem has been the propensity for microorganisms to grow in once sterile bandage material.

A major function of surgical bandages and packing materials is the absorption of various excreted fluids. These fluids are frequently rich in nutrients and are capable of supporting abundant bacterial growth. Since the surgical opening or skin surface is rarely absolutely free of bacteria, the bandage material soon supports a burgeoning bacterial population. These bacteria can easily cause serious infection and may also release a variety of harmful toxins. The obvious solution to such a problem is to change the bandage material often so that bacterial buildup does not occur. An additional approach is to treat the bandage material with some type of disinfectant to limit bacterial growth. Unfortunately, it has proven difficult to produce an effective disinfectant that does not readily wash out of the material. Such wash out, or leaching, reduces effectiveness and may cause irritation or damage to body tissues.

This problem is not limited to bandages, dressings or packings for wounds or surgical incisions. There are a number of instances where absorptive packings are placed in natural body orifices with significant possibility for dangerous bacterial growth. Various nasal packings can become bacterially laden following insertion into nasal passageways. Numerous deaths have resulted from "toxic shock syndrome" resulting from multiplication of *Staphylococcus aureus* bacteria in feminine care products, particularly tampons. There have been a large number of related problems. For example, U.S. Pat. No. 5,641,503, to Brown-Skrobot, seeks to produce a germicidal tampon and contains a useful list of references to the toxic shock problem. A particular difficulty has been that many potent germicidal agents, e.g. iodine, are partially or totally ineffective in the presence of protein rich solutions such as blood or menses.

In addition, due to the globalization of commerce, the emergence of new diseases, the risks of biological warfare, the contamination of food products with highly pathogenic strains of bacteria, and other forces on society, the uses for a technology that imparts a non-leaching antimicrobial coating to a variety of surfaces is duly recognized. Specific areas of use in addition to bandage material are described below in the Summary of the Invention section.

In connection with the care and treatment of wounds, the term "wound" is meant to include burns, pressure sores, punctures, ulcers and the like. For a long time, one critical aspect of wound care has been the consideration of the requirements of the epithelium, i.e., that area of new cell growth directly peripheral to the wound which is formed during the healing process, so that healing is facilitated.

Since it has been recognized that healing of the wound occurs in one sense as the epithelium migrates by growth from the periphery inward, care has been taken not to damage unnecessarily or to irritate this new area of growth or existing, compromised periwound tissue. With many dressings, problems can occur during dressing changes. This is particularly true where the dressing adheres to the epithelium or where granulation tissue and new cell growth become intertwined within the matrix of a dressing. In these instances, there is a risk that removal of the dressing will damage the sensitive tissue and new growth on the periphery of the wound thereby causing a regression in the progress of wound healing.

Another consideration in wound care is the frequency of dressing changes. The time frame for the changing of dressings depends on many concerns and therefore opinions as to how often dressings should be changed vary drastically.

Still, another important consideration in wound care is the needs of the surrounding unwounded skin. The unwounded skin beyond the epithelium is usually in contact with some portion of the wound dressing system which maintains the dressing positioned on the wound. For example, the surrounding skin may be covered for extended periods with a wrap and/or adhesive to hold the dressing in place. Many such dressings can irritate this surrounding skin and compound problems to the patient. This is especially true in the area of leg ulcers wherein the surrounding skin can easily become sensitized by strong medicaments and is often plagued with flaking, scaling and eczema.

One type of treatment presently used, in particular for leg ulcers, comprises the application of gauze to the ulcer and the utilization of a compression wrap to secure the gauze to the ulcer. Since the gauze quickly becomes saturated, frequent changes are necessary and damage to the epithelium and surrounding skin may occur. Moreover, if the gauze is left on for too long a period, the exudate can begin to overly hydrate and macerate the patient's surrounding skin.

A second type of treatment, also used in particular for leg ulcers, is the Unna's Boot (commercially available from Biersdorf, Inc.) which comprises a zinc paste-containing bandage wrapped around a patient's leg from above the toes to below the knee. Other Unna's Boot/zinc impregnated treatments are available from Miles and Graham Field. These dressings are typically left in place for a week at a time and absorbent pads must be applied to the outside of the dressings in the area of the ulcer to absorb excess exudate. Seepage of exudate throughout the wrap is common, and damage to the skin and epithelium is inevitable.

Another type of wound dressing is disclosed in U.S. Pat. No. 5,106,362 to Gilman. This dressing is provided with a base sheet for contacting the skin of a patient. The base sheet has an opening for placement over the wound. The dressing has a vent for providing controlled leakage of fluid along a path from the wound through the opening of the base sheet.

The vent is designed to provide control over wound leakage along a "tortuous path" from the wound through the opening of the base sheet.

A modification of the dressing of U.S. Pat. No. 5,106,362 is disclosed in U.S. Pat. No. 5,056,510, also to Gilman. The '510 patent discloses a vented dressing where the fabric reservoir for wound exudate is contained within a chamber. The walls of the chamber are intended to provide a barrier to bacterial and other contaminants. The walls of the chamber are also intended to be air permeable so as to permit egress of air from the voids of the fabric reservoir. These Gilman dressings do not especially address the problems of the epithelium and the surrounding skin.

It is apparent that, considering the various types of wounds, the numerous dressings that are available, and the various stages of healing, there is still a tremendous need for a dressing that functions better than the current dressings, especially with respect to preventing damage to surrounding skin, tissue and new cell growth. In particular, a wound dressing system which protects the epithelium and surrounding non-wounded skin, which wicks away moisture from the wound area, and which does not purposely adhere to the wound or the surrounding area would be a useful addition to the wound care art. A dressing for patients with fragile skin surrounding a wound would be especially beneficial.

Certain wound dressing materials have been used to absorb exudate and promote healing. For example, Mason, et al., U.S. Pat. No. 4,393,048 teaches a hydrogel composition which, when applied as a powder, absorbs wound exudate. The hydrogel formation may not be complete and lumps of partially hydrated powders form which, when removed, may reopen the wound.

It is known that wounds heal more rapidly and completely if kept in a slightly moist or hydrated state. Polyethylene glycol containing hydrogel wound coverings are disclosed in U.S. Pat. No. 4,226,232, to Spence. These hydrogels cannot be sterilized by irradiation due to the formation of free radicals.

Rawlings et al., U.S. Pat. No. 4,657,006, illustrates wound dressings comprised of a hydrophilic polymer having moisture and vapor permeability properties. However, the exudate absorbed by the hydrophilic polymer tends to harden or solidify the polymer.

An ideal wound dressing should not only absorb exudate but also possess antimicrobial or antibacterial properties. As used in this disclosure, "antibacterial" is defined as having an adverse effect on bacteria, particularly disease-causing bacteria. Furthermore, "antimicrobial" is defined as having an adverse effect on a range of microorganisms, including bacteria and at least some fungi and viruses. An antimicrobial wound dressing is generally preferred over an antibacterial wound dressing.

One example of an antimicrobial wound dressing is Matson, U.S. Pat. No. 4,728,323, which discloses a wound dressing comprising a substrate coated with a coating of a silver salt that allegedly also keeps the wound moist. Since the active agent (silver ion) is not covalently bound to the dressing material, there is a potential for leaching into the body and/or depletion of the active agent.

In the past, wounds have been treated with antimicrobial active agents applied to the wound and covered with a covering that inhibits the healing process. For example, it was conventional practice early in the 20th Century to apply an antiseptic mercury agent such at thimerosal (Merthiolate) or merbromin (Mercurochrome) and the like to a wound and then cover or wrap the wound with a bandage such as gauze or an adhesive strip having a central absorbent gauze portion. A disadvantage of this approach is that the wound often weeps or exudes fluids such as blood, pustulation and the like. While the gauze may absorb some of these fluids, the gauze often adheres to the wound such that removal of the dressing reopens the wound. Advances in the art have been made in both bandages and antimicrobial agents. Certain bandages now contain a nonadhering polymeric coating over or, in place of, the gauze that inhibits the adhering of the absorbent material to the wound but also inhibits the absorption of the exudate that is necessary to properly heal the wound.

Korol, U.S. Pat. No. 4,563,184, discloses wound dressings comprising a polymer, such as poly(2-hydroxyethyl-methacrylate), a solvent, such as polyethylene glycol, and a plasticizer such as DMSO. An antimicrobial agent, such as silver sulfadiazine, may be incorporated into the polymeric material.

Widra, U.S. Pat. No. 4,570,629, is drawn to absorbent hydrogel membrane wound dressings made up of hydrophilic biopolymeric copolyelectrolytes comprising a water-soluble linear anionic protein polyelectrolyte component derived from keratin and a water-soluble linear cationic biopolymer polyelectrolyte component derived from either collagen or a glycosaminoglycan. The membranes may also contain antibiotics.

Klemm et al., U.S. Pat. No. 4,191,743, teach the administration of antibiotics to wounds using a wound dressing comprising at least two layers of synthetic resin arranged one above the other having an intermediate layer composed of a synthetic resin granulate having an antibiotic incorporated therein.

Hansen et al., U.S. Pat. No. 5,498,478 is directed to the use of a polyethylene glycol or similar polymer as a binder material for fibers of any variety. The binder and fibers may be pretreated by slurrying the fibers in baths containing antimicrobial agents as part of the solution, thereby causing the fibers and the subsequently formed matrix of polymer and fibers to have an antimicrobial ability.

Mixon et al., U.S. Pat. No. 5,069,907 is directed to the formation and use of a polymeric sheet which may include an antimicrobial agent. This patent teaches of the inclusion of antimicrobial agents into either a pressure-sensitive layer, such as an adhesive, or in a drape used to cover a wound or other sensitive area.

Dietz et al., U.S. Pat. Nos. 5,674,561 and 5,670,557 are directed to polymerized microemulsion pressure sensitive adhesive compositions that may optionally contain antimicrobial and/or other biologically active agents. The potential antimicrobial activity of quaternary amine and quaternary ammonium salts is taught. It is further taught that an antimicrobial agent can be added so as to be contained in a specific layer of a pressure sensitive adhesive device for use as a medical skin covering and/or as a wound dressing.

Young et al., U.S. Pat. No. 5,432,000, teach the use of a polymeric network for adhering particulate materials to a fiber or fibrous product. Specifically, this patent teaches of the use of polymers, such as polyethylene glycol or polyethylene to cause the binding of particulate materials to a fiber, such as cloth. One such particulate member which could be adhered to cloth is an antimicrobial agent, such as epoxide phenol or another antimicrobial substance.

U.S. Pat. No. 5,811,471, to Shanbrom, teaches immobilization of germicidal dyes such as methylene blue onto polyvinyl alcohol gels. The dyes are not covalently bound; however, and thus have the potential to be desorbed. This potential shortcoming is discussed in '471: "Even though dyed PVA appears non-irritating, there might be some concern that the disinfectant dye molecules could migrate to human tissue in contact with the material". Another potential drawback discussed therein is that the dyes are strongly colored, and hence may not be visually appealing to the consumer: "In the case of some products like tampons a "clean" white product might be psychologically more acceptable".

In U.S. Pat. No. 4,643,181, Brown discusses mixing an antimicrobial biguanide compound with an adhesive. The adhesive polymer is incorporated into the system to bind the biguanides (which are desorbed from the non-woven material when it is wetted by urine. It is clear from the data that the biguanide antimicrobial leaches from the material, and thus it is a drug-releasing system.

A number of antimicrobial systems based on leaching of low concentrations of silver ion from surfaces have also been reported. For instance, U.S. Pat. Nos. 6,126,931 and 6,030,632 describe a biguanide polymer (PHMB) bonded a substrate. Silver salts are then bonded to the immobilized PHMB. The surface-bound PHMB alone does not inhibit bacterial growth, but it does bind the bacteria, thus allowing the low-solubility silver salts to function.

A similar invention is reported in U.S. Pat. No. 5,662,913, to Capeli, wherein wound dressings which contain silver salts are discussed. The silver is stabilized by polyether polymers.

Another similar method is described in U.S. Pat. No. 5,856,248, to Weinberg, except that copper salts are used instead of silver.

The leaching of silver from elemental silver coatings on medical textiles is described by Tweden et al. ("Silver Modification of Polyethylene Terephthalate Textiles for Antimicrobial Protection"; ASAIO Journal, 43, pM475-M481 (1997). In that study the leaching of silver was equivalent to a serum silver concentration of 55 ppb in an adult human of normal blood volume.

In U.S. Pat. No. 5,985,301, Nakamura describes cellulose fiber that contains silver as an antibacterial agent. In short, cellulose is dissolved in a particular type of solvent, and then silver compounds are added. Fibers are then spun from these solutions. It is reported that these fibers have bactericidal properties. This method must be considered a drug-releasing technology. This fact is emphasized by the following quote from the Nakamura patent: " . . . enhancing antibacterial effects presumably by promoting the discharge of silver ions from the silver-based antibacterial agent."

It is known that certain quaternary ammonium salts possess antimicrobial properties. Examples include benzethonium chloride and benzalkonium chloride (BACTINE). It is also known that certain low molecular weight quaternary ammonium groups can be incorporated into polymeric substrates (without chemical bonding) in order to provide certain degrees of antimicrobial activity.

Ionene polymers or polymeric quaternary ammonium compounds (polyquats), i.e., cationic polymers containing quaternary nitrogens in the polymer backbone, belong to a well-known class of biologically-active compounds. See, e.g., A. Rembaum, Biological Activity of Ionene Polymers, Applied Polymer Symposium No. 22, 299-317 (1973). Ionene polymers have a variety of uses in aqueous systems such as microbicides, bactericides, algicides, sanitizers, and disinfectants. U.S. Pat. Nos. 3,778,476, 3,874,870, 3,898,336, 3,931,319, 4,013,507, 4,027,020, 4,089,977, 4,111,679, 4,506,081, 4,581,058, 4,778,813, 4,970,211, 5,051,124, and 5,093,078 give various examples of these polymers, their preparation, and their uses. U.S. Pat. Nos. 3,778,476, 3,898,536, and 4,960,590, in particular, describe insoluble tri-halide containing ionene polymers. U.S. Pat. No. 4,013,507 describes ionene polymers which selectively inhibit the growth of malignant cells in vitro.

Hou et al., U.S. Pat. No. 4,791,063, teach polyionene-transformed modified polymer-polysaccharide separation matrices for use in removing contaminants of microorganism origin from biological liquids. This patent teaches that absorption of bacterial cells by ion-exchange resins is attributable to electrostatic attraction between quaternary ammonium groups on the resin surface and carboxyl groups on the bacteria cell surface.

Chen et al. describe the preparation of antimicrobial dendrimers (highly-branched polymers) having quaternary ammonium functionality (Chen, et al., "Quaternary Ammonium Functionalized Poly(propylene imine) Dendrimers as Effective Antimicrobials: Structure-Activity Studies", Biomacromolecules 1 p 473-480 (2000)). The compounds described therein are soluble in water; hence, they are not suitable for use as wound dressing materials. The enhanced antimicrobial properties exhibited by polymeric quaternary compounds (relative to monomeric quats), is discussed therein, and also in several other references (Ikeda, T., "Antibacterial Activity of Polycationic Biocides", Chapter 42, page 743 in: High Performance Biomaterials, M. Szycher, ed., Technomic, Lancaster Pa., (1991); Donaruma, L. G., et al., "Anionic Polymeric Drugs", John Wiley & Son, New York, (1978); Ikeda T, Yamaguchi H, and Tazuke, S "New Polymeric Biocides Synthesis and Antibacterial Activities of Polycations with Pendant Biguanide Groups"; Antimicrob. Agents Chemother. 26(2), p 139-44 (1984)).

U.S. Pat. No. 6,039,940, to Perrault, teaches a composition and method for treating a wound with an inherently antimicrobial dressing based on quaternary ammonium polymers. The dressing is a hydrogel containing, by weight, about 15 to 95 percent, and preferably about 61 to 90 percent, and most preferably about 65 to 75 percent, cationic quaternary amine acrylate polymer. This polymer is prepared by the polymerization of acryloyloxyethyl(or propyl)-trialkyl(or aryl)-substituted ammonium salts or acrylamidoethyl(or propyl)-trialkyl(or aryl)-substituted ammonium salts. Ultraviolet light is used as the catalyst. The antimicrobial hydrogels are stated to be non-irritating to the wound, absorb wound exudate, and, due to the inherently antimicrobial properties, "enhance the sterile environment around the wound."

However, the human trial detailed in the '940 disclosure concluded that the measured parameter, the 'irritation potential', was "not significantly different from the control". Analysis of the numerical results indicate that no hydrogel dressing tested gave a better improvement during the test period than the control. This suggests that the use of a hydrogel, although providing a "soothing effect" according to the '940 patent, may not be the optimum dressing for wound healing. Also, it is believed that the present invention offers an advantage over dressing such as the '940 dressing in that the dressing of the present invention are applied a non-gel dressings (e.g., they are dry rather than hydrated). This provides a greater potential for uptake of wound exudates and other aqueous solutions, compared to the '940 hydrogels, which already have water occupying sites in the composition.

Also, the polymers described in the '940 patent are based on acrylate or acrylamide, and as such are susceptible to hydrolysis. Hydrolysis is expected to be greater at high pH or at low pH. It should be noted that these materials are hydrogels, and thus contain a significant amount of water (e.g., 5% to 85%). It also states that the hydrogels are preferably prepared with a physical support structure in order to better retain the hydrogel over a wound. Although the possibility of forming these hydrogels around a web or fibril support is given, it is not clear that the hydrogel material is bonded to the support in any manner. The materials can be dried to powders and later reconstituted. The fact that the hydrogel materials are powders when dry would indicate that shedding of loose hydrogel particles is to be expected. A device wherein the absorbent material is permanently bound to a structural substrate would be more desirable.

The hydrogel materials described by the '940 patent are not breathable. That is, they do not permit unrestricted passage of air through the samples. In that method, the spaces between strands of the "support material" are essentially clogged by hydrated hydrogel material. In the current invention, the individual filaments and fibrils within the substrate are separately "coated" with covalently-bonded antimicrobial polymer. Note that this can be achieved even on a basic raw material such as cotton lint, or wood pulp, which can then be formed into a fabric or other useful structure. Such a process is not possible with the technology described by the '940 patent. In that case, the non-bonded composite must be formed over a prefabricated structure which is a time-consuming process.

The '940 patent also teaches that residual monomer concentrations of up to 3% are acceptable. Such a high level of residual monomer would undoubtedly result in release of active antimicrobial agent into a wound. Monomers such as those used to produce the hydrogels described in the '940 patent are known to cause skin and eye irritation, as well as sensitization (MSDS #14491: Ciba Specialty Chemicals Corporation). While not being bound to a particular theory, another source of leaching of antimicrobial activity may be poor or incomplete cross linking; this may be a source of leaching in that the polymers are only linked to one another, rather to a substrate. It is also difficult and time-consuming to completely wash a hydrogel in order to extract all residual monomer and other leachables without destroying the network structure. The leaching may become greater or less based on ambient conditions of wound exudate. Evidence of leaching from the hydrogel composition are in the '940 patent's summary of the Kirby-Bauer zone of inhibition data. That data, presented in Table 1 of the '940 patent, demonstrate large zones of inhibition, up to 20 mm, around a 5 mm square hydrogel sample. While the '940 patentees meant this data to indicate the antimicrobial effectiveness of the hydrogel, a proper interpretation, in comparison with the non-leaching attributes of the present invention, indicates that the '940 compositions demonstrate a drug-releasing/leaching phenomenon.

In conclusion with regard to the above descriptions of the art, it is apparent that there is a need for an improved dressing that has an effective antimicrobial coating or layer on it, which is covalently bound to a substrate, and is non-leaching upon use.

The antimicrobial activity of a polystyrene fiber containing covalently bonded tertiary amine groups was tested by Endo et al. ("Antimicrobial Activity of Tertiary Amine Covalently Bonded to a Polystyrene Fiber", Applied Journal of Environmental Microbiology 53(9), p 2050 (1987). Only very slight antimicrobial activity was found for these fibers in the absence of other agents. Significant antimicrobial activity was only observed when these fibers were combined with other antimicrobial agents such as deoxycholate or actinomycin (leachable antibiotics). The material described is based on polystyrene, and thus it is not expected to have physical properties suitable for an absorbent wound dressing material.

The cerium (IV) ion initiated graft polymerization of vinyl monomers onto hydroxyl-containing substrates was first described by Mino (G. Mino and S. Kaizerman; "A New Method for the Preparation of Graft Copolymers. Polymerization Initiated by Ceric Ion Redox Systems", Journal of Polymer Science 31(22), p 242 (1958)). The mechanism and kinetics of Ce(IV)-initiated graft polymerization of vinylacetate-acrylonitrile onto PVA in water solution was studied by Odian and Kho (G. Odian and J. H. T. Kho; "Ceric Ion Initiated Graft Polymerization onto Poly(vinyl Alcohol)", J. Macromolecular Science—Chemistry A4(2) p 317-330, (1970)). Later, Vitta et al. described the grafting of methacrylic acid onto solid cellulose substrates (S. B. Vitta, et al., "The Preparation and Properties of Acrylic and Methacrylic Acid Grafted Cellulose Prepared by Ceric Ion Initiation. Part I. Preparation of the Grafted Cellulose", J. Macromolecular Science—Chemistry A22(5-7) p 579-590 (1985)). None of these references describe antimicrobial materials, or graft polymers based on quaternary ammonium compounds.

A large number of other inventors have labored to produce germicidal bandage and packing materials. U.S. Pat. No. 5,441,742 to Autant et al. discloses a modified cellulosic material with biocidal properties. Unfortunately, water releases the biocidal agents from the material with the concomitant problems of irritation or toxicity towards surrounding tissues. Iodine has been a favored biocidal material. Both U.S. Pat. No. 5,302,392 to Karakelle et al. and U.S. Pat. No. 5,236,703 to Usala rely on polymers containing polyvinylpyrrolidone to bind and release iodine. Another approach is shown in U.S. Pat. No. 5,091,102 to Sheridan which relies on the presence of a cationic surfactant to provide germicidal properties to a dry fabric. All of these inventions suffer the problem of having a more or less toxic germicide that can leach from the material.

All patents, patent applications and publications discussed or cited herein are understood to be incorporated by reference to the same extent as if each individual publication or patent application was specifically and individually set forth in its entirety.

From the above review, it is apparent that what is needed in the art of would dressings is a broad spectrum antibacterial or antimicrobial agent that remains in the bandage material where it can prevent bacterial growth, without exerting any negative effects on adjacent living tissue. Similarly, a need also exists for other products to have non-leaching, antibacterial or antimicrobial surfaces to act prophylactically to prevent or reduce the presence of pathogens on such surfaces. Specific examples of such applications of the present technology are provided in the following section.

SUMMARY OF THE INVENTION

The present invention provides methods and compositions for an antimicrobial and/or antibacterial composition comprising a substrate over which a non-leaching polymeric coating is covalently bonded. The polymeric coating contains a multitude of quaternary ammonium groups which exert activity against microbes, and also is absorptive of aqueous solutions. A preferred method of fabrication is also described.

One object of the present invention is to make a wound dressing that comprises an absorbent, non-leaching antimicrobial surface over a suitable dressing substrate. A typical substrate is cellulose or other fibrous mesh, such as a gauze pad. Surprisingly, tests have proved that certain novel forms of polymers on a wound dressing substrate, while not rising to the definition of "superabsorbent" in the parent application, are in fact highly effective at reducing or eliminating the numbers of microbes, including fungi and viruses in addition to a range of bacteria. These embodiments have been shown to be non-leaching. It has also been shown that such materials can be produced on a variety of substrates without significant changes in the physical properties of the substrates such as texture, color, odor, softness, or mechanical strength. Another object of the present invention is a superabsorbent polymer material having antibacterial properties. Another embodiment of the present invention demonstrates the effectiveness of such a superabsorbent polymer.

Another object of the present invention is a composition that comprises a substrate with a covalently bonded superabsorbent polymer surface having antimicrobial properties, which is covered or surrounded by a second substrate to which is covalently bonded another layer of polymer which is not superabsorbent, but which does have a high level of antimicrobial groups. This combination provides both high capacity of liquids absorption, and a high level of antimicrobial activity, while maintaining the feel and handling characteristics of a conventional fabric, particularly in the preferred configuration in which the outermost layer is the non-superabsorbent polymer described herein.

Another object of the invention is the inclusion in a dressing or pad according to the present invention of an indicator that indicates a condition or the status of the recipient based on some aspect of fluid or other input from the user. For instance, an indicator (such as a color indicator) on a wound dressing may indicate the type of infection or the presence of HIV antibodies, and an indicator (such as a color indicator) on a tampon or like pad may indicate whether or not the user is pregnant, or her HIV status.

Another object of the present invention is to provide methods and compositions that pertain to antimicrobial surfaces for a variety of supplies and equipment, including a sanitary pad, a tampon, a diaper, a sponge, a sanitary wipe, food preparation surfaces, and other surfaces in need of a non-leaching antimicrobial property.

DETAILED DESCRIPTION OF THE INVENTION

Definitions

For the purposes of this disclosure, certain definitions are provided. By "non-hydrolyzable" is meant a bond that does not hydrolyze under standard conditions to which a bond is expected to be exposed under normal usage of the material or surface having such bond. For instance, in a wound dressing according to the present invention that has "non-hydrolyzable" bonds, such "non-hydrolyzable" bonds do not hydrolyze (e.g., undergo a hydrolysis-type reaction that results in the fission of such bond) under: normal storage conditions of such dressing; exposure to would exudates and/or body fluids when in use (e.g., under exposure to an expected range of pH, osmolality, exposure to microbes and their enzymes, and so forth, and added antiseptic salves, creams, ointments, etc.). The range of such standard conditions are known to those of ordinary skill in the art, and/or can be determined by routine testing.

By "non-leaching" is meant that sections of the polymer of the present invention do not appreciably separate from the material and enter a wound or otherwise become non-integral with the material under standard uses. By "not appreciably separate" is meant that no more than an insubstantial amount of material separates, for example less than one percent, preferably less than 0.1 percent, more preferably less than 0.01 percent, and even more preferably less than 0.001 percent of the total quantity of polymer. Alternately, depending on the application, "not appreciably separate" may mean that no adverse effect on wound healing or the health of an adjacent tissue of interest is measurable.

In regard to the above, it is noted that "non-leachable" refers to the bond between the polymer chain and the substrate. In certain embodiments of the present invention, a bond between the polymer backbone and one or more type of antimicrobial group may be intentionally made to be more susceptible to release, and therefore more leachable. This may provide a benefit where it is desirable for a percentage of the antimicrobial groups to be selectively released under certain conditions. However, it is noted that the typical bond between the polymer chain and antimicrobial groups envisioned and enabled herein are covalent bonds that do not leach under standard exposure conditions.

Polymers according to the present invention have the capacity to absorb aqueous liquids such as biological fluids (which are defined to include a liquid having living or dead biologically formed matter, and to include bodily fluids such as blood, urine, menses, etc.). The capacity to absorb an aqueous liquid can be measured by the grams of water uptake per gram of absorbent material in a single instance. One general definition for a superabsorbent polymer is that such polymer generally would be capable of absorbing, in a single instance, about 30 to 60 grams of water per gram of polymer. A broader definition could include polymers that absorb less than 30 grams of water per gram of polymer, but that nonetheless have enhanced capacity to absorb water compared to similar materials without such enhanced capacity. Alternately, an "absorbent" as opposed to a "superabsorbent" polymer may be defined as a polymer that has a capacity to absorb aqueous liquids, but which normally will not absorb over 30 times its weight in such liquids.

By "degree of polymerization" is meant the number of monomers that are joined in a single polymer chain. For example, in a preferred embodiment of the invention, the average degree of polymerization is in the range of about 5 to 1,000. A more preferred average degree of polymerization is in the range of about 10 to 500, and an even more preferred average degree of polymerization is in the range of about 10 to 100.

Finally, a substrate is defined as a woven or nonwoven, solid, or flexible mass of material upon which the polymers of the invention can be applied and with which such polymers can form covalent bonds. Cellulose products, such as the gauze and other absorbent dressings described in the following paragraphs, are preferred materials to be used as water-insoluble bases when a wound dressing is prepared. The term "substrate" can also include the surfaces of large objects, such as cutting boards, food preparation tables and equipment, surgical room equipment, floor mat, blood transfer storage container, cast liner, splint, air filter for autos, planes or HVAC systems, military protective garment, face mask, devices for protection against biohazards and biological warfare agents, lumber, meat packaging material, paper currency, and other surfaces in need of a non-leaching antimicrobial property, and the like, onto which is applied the antimicrobial polymeric coating in accordance with the present invention. Apart from cellulose, any material (ceramic, metal, or polymer) with hydroxyl groups on it's surface can be used as a substrate for the cerium (IV) catalyzed grafting reaction described in the following paragraphs. The extent of grafting will be dependent on the surface hydroxyl concentration. Even materials which do not normally contain sufficient surface hydroxyl groups may be used as substrates, as many methods are available for introducing surface hydroxyl groups. These methods generally include hydrolysis or oxidation effected by methods such as heat, plasma-discharge, e-beam, UV, or gamma irradiation, peroxides, acids, ozonolysis, or other methods. It should be noted that methods other than cerium initiated grafting may also be used in the practice of this invention.

Various materials were investigated by the inventors as substrates for the preparation of absorbent dressings containing covalently-bonded, polymeric quaternary ammonium biocidal agent. Among these materials were several commercially-available gauze and surgical sponge products, including several materials manufactured by Johnson & Johnson Company (J&J). J&J's, "NU GAUZE", General use sponge (referred to in this application as "sub#1"), J&J's "STERILE GAUZE Mirasorb sponge" (herein referred to as "sub#4"), and J&J's "SOFT WICK" dressing sponge (herein referred to as "sub#5") were all used to prepare working prototypes. All three materials are rayon/cellulose (sub #4 also contains polyester) sheets with non-woven mesh-like structures, and a fiber surface area much greater than traditional woven cotton-fiber gauze. Sub#1 and sub#4 are a single 8"×8" sheet which is folded into a 4-layer sheet measuring 4"×4", and both weigh approximately 1.45 to 1.50 grams per sheet. Sub#5 has a denser structure, and is made from a single 12"×8" sheet folded into a 6-layer sheet measuring 4"×4", weighing approximately 2.5 grams.

In addition, several types of fabric materials were also used as substrates, including: "Fruit of the Loom" 100% cotton knitted tee-shirt material, "Gerber" 100% cotton bird's-eye weave cloth diaper material, "Cannon" 100% cotton terry wash-cloth material, "Magna" yellow, non-woven wiping cloth (75% rayon, 25% polyester), and "Whirl" cellulose kitchen sponge"; referred to herein as: "subTS", "subDIA", "subWC", "subMag", and "subCKS" respectively. The scope of this invention is not limited to the use of materials mentioned herein as substrates.

Modification of these substrates to prepare absorbent materials with antimicrobial properties was achieved by immersing the substrates into aqueous solutions of vinyl monomers containing quaternary ammonium groups. Reaction of these monomers with the substrate materials to form graft polymers was catalyzed by ceric ion (Ce.sup.+4). A typical modification procedure is detailed in Example 1. Other samples were prepared according to the same basic procedure; however, different substrates, monomers, reaction conditions, washing/drying procedures were used. This data is summarized in Table 1.

Additionally, another aspect of the present invention is the inclusion in a dressing of a hemostatic agent. Hemostatic compounds such as are known to those skilled in the art may be applied to the dressing, either by bonding or preferably added as a separate component that dissolves in blood or wound exudates, and acts to reduce or stop bleeding.

Finally, a substrate is defined as a woven or nonwoven, solid, or flexible mass of material upon which the polymers of the invention can be applied and with which such polymers can form covalent bonds. Cellulose products, such as the gauze and other flexible absorbent dressings described in the following paragraphs, are preferred materials to be used as flexible substrates when a wound dressing is prepared. The term "substrate" can also include the surfaces of large, generally non-flexible objects, such as cutting boards, food preparation tables and equipment, and surgical room equipment, and other large flexible or generally non-flexible objects such as a floor mat, a blood transfer storage container, a cast liner, a splint, air filters for autos, planes or HVAC systems, military protective garment, face mask, devices for protection against biohazards and biological warfare agents, lumber, meat packaging material, paper currency, and other surfaces in need of a non-leaching antimicrobial property, and the like, onto which is applied the antimicrobial polymeric coating in accordance with the present invention. Apart from cellulose, any material (ceramic, metal, or polymer) with hydroxyl groups on it's surface can be used as a substrate for the cerium (IV) catalyzed grafting reaction described in the following paragraphs. The extent of grafting will be dependant on the surface hydroxyl concentration. Even materials which do not normally contain sufficient surface hydroxyl groups may be used as substrates, as many methods are available for introducing surface hydroxyl groups. These methods generally include hydrolysis or oxidation effected by methods such as heat, plasma-discharge, e-beam, UV, or gamma irradiation, peroxides, acids, ozonolysis, or other methods. It should be noted that methods other than cerium initiated grafting may also be used in the practice of this invention.

EXAMPLE 1

Production of Absorbent Anti-Microbial Compounds

A commercially available surgical sponge rayon/cellulose gauze material (sub#4) was unfolded from its as-received state to give a single layer sheet measuring approximately 8" by 8". The sample was then refolded "accordion-style" to give a 6-layer sample measuring approximately 1.33" by 8". This was then folded in the same manner to give a 24-layer sample measuring approximately 1.33" by 2". This refolding was done so as to provide uniform and maximum surface contact between the substrate and reaction medium, in a small reaction vessel. A solution was prepared by mixing 0.4 grams of ammonium cerium (IV) nitrate (CAN) (Acros Chemical Co. cat #201441000), 25.0 mL [2-(methacryloyloxy)ethyl]trimethylammonium chloride (TMMC) (Aldrich Chemical Company, cat#40, 810-7), and 55 mL of distilled water. This solution was placed into a 250 mL wide-mouth glass container equipped with a screw-cap lid, and argon gas was bubbled vigorously through the solution for 60 seconds. The folded gauze substrate was placed into the solution, and the solution was again sparged with argon for 30 seconds. The container was capped while being flushed with a stream of argon gas. The container was placed into an oven set at 75° C., and gently agitated by hand every 30 minutes for the first two hours, then every hour for the next 4 hours. After a total of 18 hours, the jar was removed from the oven and allowed to cool to room temperature. The sample was removed from the jar, unfolded, and thoroughly washed three times with water, being allowed to soak in water for at least 30 minutes between washings. These sequential washings, also termed rinsings, remove effectively all of the non-polymerized monomer molecules, non-stabilized polymer molecules, and catalyst, such that the final composition is found to not leach its antimicrobial molecules, by routine detection means known and used by those of ordinary skill in the art. By non-stabilized polymer molecules is meant any polymer molecule that has neither formed a covalent bond directly with a binding site of the substrate, nor formed at least one covalent bond with a polymer chain that is covalently bonded (directly or via other polymer chain(s)) to the substrate.

After these rinsings, excess water was removed from the sample by gently squeezing. Further dewatering was accomplished by soaking the sample in 70% isopropanol for 30 minutes. Excess alcohol was removed by gently squeezing the sample, which was then allowed to dry overnight on a paper towel in open air. The sample was then dried in vacuum at room temperature for 18 hours. The sample was allowed to stand in air for 15 minutes before being weighed. The final weight of the sample was measured to be 2.13 grams. The initial weight of the sample before treatment was 1.45 grams. The percent of grafted polymer in the final product was calculated as follows (2.13−1.45)/2.13×100=31.9%. Some disruption of the fiber packing of the mesh structure was observed, and this resulted in a "fluffier" texture for the treated material.

Preparations of additional samples were performed according to similar procedures using different substrates, antimicrobials and reaction conditions. The reaction conditions and percent grafting data for each sample are summarized in Table 1.

All procedures were performed in 500 mL or 250 mL screw-cap glass jars overnight (approximately 18 hours), except for samples #43-45 which were reacted for indicated times.

The samples prepared as shown in Table 1 indicated that high-yield grafting of vinyl monomers containing quaternary ammonium groups onto various textile substrate materials can be achieved under rather mild conditions. The appearance

TABLE 1

Ceric ion initiated grafting of gauze substrates

| Sample # | Substrate | Monomer | [Monomer] (mol/L) | [Ce+](mM) | T (° C.) | Total Vol. | % Grafting |
|---|---|---|---|---|---|---|---|
| 1 | #4 | TMMC | 1 | 11 | 75 | 80 mL | 12% |
| 2 | #1 | TMMC | 1.2 | 14 | 75 | 80 mL | 34% |
| 3 | #1 (x2) | TMMC | 1.2 | 14 | 75 | 80 mL | 32% |
| 4 | #1 | TMMC | 1.2 | 9 | 75 | 80 mL | 32% |
| 5 | #1 (x2) | TMMC | 1.2 | 9 | 75 | 80 mL | 20% |
| 6 | #1 | TMMC | 0.7 | 14 | 75 | 80 mL | 28% |
| 7 | #1 (x2) | TMMC | 0.7 | 14 | 75 | 80 mL | 27% |
| 8 | #1 | TMMC | 1 | 11 | 75 | 80 mL | 37% |
| 9 | #1 | TMMC | 1 | 11 | 75 | 80 mL | 37% |
| 10 | #1 | TMMC | 1.2 | 11 | 75 | 80 mL | 25% |
| 11 | #1 | TMAPMC | 1.2 | 10 | 75 | 90 mL | <1% |
| 12 | #1 | TMAS | 0.9 | 11 | 75 | 80 mL | 20% |
| 13 | #1 | DADMAC | 1.4 | 10 | 75 | 90 mL | 6% |
| 14 | #4 (x2) | TMMC | 1.3 | 15 | 90 | 60 mL | Degraded |
| 15 | #4 (x2) | TMMC | 0.5 | 11 | 90 | 85 mL | 5% |
| 16 | #4 (x2) | TMMC | 0.7 | 15 | 90 | 60 mL | 13% |
| 17 | #4 | TMMC | 0.7 | 15 | 90 | 60 mL | 9% |
| 18 | #1 | TMMC | 1.3 | 15 | 90 | 60 mL | Degraded |
| 19 | #1 | TMMC | 0.7 | 15 | 90 | 60 mL | 23% |
| 20 | #1 | TMMC | 0.4 | 15 | 90 | 60 mL | 17% |
| 21 | #4 | TMMC | 1.3 | 15 | 90 | 60 mL | 26% |
| 22 | #4 | TMMC | 0.7 | 8 | 75 | 60 mL | 7% |
| 23 | #1 | TMMC | 2 | 20 | 75 | 60 mL | 30% |
| 24 | #1 | TMMC | 2 | 5 | 75 | 60 mL | <1% |
| 25 | #1 | TMMC | 0.7 | 20 | 75 | 60 mL | 25% |
| 26 | #1 | TMMC | 0.7 | 7 | 75 | 60 mL | 15% |
| 27 | #1 | TMAS | 0.4 | 7 | 60 | 200 mL | 14% |
| 28 | #1 | TMAS | 0.2 | 2 | 60 | 200 mL | 11% |
| 29 | #1 | TMAS | 0.8 | 10 | 60 | 200 mL | 19% |
| 30 | #1 | TMMC | 1 | 11 | 50 | 80 mL | 44% |
| 31 | #5 | TMMC | 1 | 11 | 50 | 80 mL | 48% |
| 32 | #5 | TMMC | 1 | 11 | 50 | 80 mL | 48% |
| 33 | #5 | VBTAC | 0.7 | 78 | 60 | 35 mL | 15% |
| 34 | #5 | DADMAC | 2 | 60 | 60 | 60 mL | 7% |
| 35 | #5 | VBTAC | 0.4 | 50 | 60 | 37 mL | 20% |
| 36 | DIA | TMMC | 0.8 | 11 | 50 | 150 mL | 12% |
| 37 | WC | TMMC | 1 | 18 | 65 | 200 mL | 22% |
| 38 | MAG | TMMC | 1 | 28 | 65 | 100 mL | 39% |
| 39 | CKS | TMMC | 0.8 | 11 | 60 | 150 mL | 11% |
| 40 | TS | TMMC | 1 | 15 | 50 | 150 mL | 17% |
| 41 | #5 | TMMC/ SR344 | 0.7 2.00% | 15 | 60 | 122 mL | 64% |
| 42 | #5 | TMMC/ SR344 | 0.4 2.00% | 15 | 60 | 224 mL | 79% |
| 43 | #5 | TMMC | 0.9 | 10 | 75 | 85 mL | 18% 30 min. |
| 44 | #5 | TMMC | 0.9 | 10 | 80 | 85 mL | 21% 15 min. |
| 45 | #5 (x2) | TMMC | 0.9 | 10 | 55 | 170 mL | 32% 2 hours |

NOTES for Table 1:
TMMC = [2-(Methacryloyloxy)ethyl]trimethylammonium chloride (75% solution in water) Aldrich Chemical #40,810-7
TMAS = [2-(Acryloyloxy)ethyl]trimethylammonium methyl sulfate (80% solution in water) Aldrich Chemical #40,811-5
TMAC = [2-(Acryloyloxy)ethyl]trimethylammonium chloride (80% solution in water) Aldrich Chemical #49,614-6
TMAPMC = [3-(Methacryloylamino)propyl]-trimethylammonium chloride (50% solution in water) Aldrich Chemical #28,065-8
VBTAC = vinylbenzyltrimethylammonium chloride Acros Chemical #42256
DADMAC = diallyldimethylammonium chloride (65% solution in water) Aldrich Chemical #34,827-9
SR344 = poly(ethylene glycol)diacrylate Sartomer Company #SR344 of the prepared biocidal absorbent dressings generally was identical to that of the starting material. Parameters such as mechanical strength, color, softness, and texture were found to be sufficient and acceptable for use in the various applications mentioned above. For instance, the materials based on medical dressings were soft, white, odorless, and absorbent. Storage of these materials for several months yielded no observable physical changes. The same holds true for heat treatments of 75° C. for several hours (this is not meant to be a limiting condition).

It should be noted that although these examples demonstrate modification of textile fabrics already in finished form, it is also within the scope of this invention to achieve the grafting modification at the raw materials stage. Threads, yarns, filaments, lints, pulps, as well as other raw forms may be modified and then fabricated into useful materials or fabrics (woven or nonwoven) by weaving, knitting, spinning, or other forming methods such as, spunbonding, melt blowing, laminations thereof, hydroentanglement, wet or dry forming and bonding, etc.

Grafting yields were found to be reproducible with constant formulation and reaction conditions. Samples were thoroughly washed to remove any residues such as unreacted monomer or homopolymer. Degree of grafting was calculated based on the weight of the starting material and the final dried weight of the grafted material. The calculated values of percent grafting are subject to a certain degree of error based upon the fact that the materials appear to contain a small amount of adsorbed water due to exposure to the laboratory atmosphere. This is true even for the untreated starting materials which were generally found to show a reversible weight loss of approximately 5 to 7% after being dried in a 60° C. oven for 30 minutes. Another potential source of error is the possibility of the presence of other counterions besides chloride (bromide, or nitrate, for instance). Experiments were conducted to correlate the weight of treated samples after washing with excess salt solutions of various composition. Related to this is the well-known observation that quaternary ammonium compounds strongly bind sodium fluorescein dye to form a colored complex. Various samples from Table 1 were tested by immersing them in a concentrated (5%) solution of sodium flourescein, followed by drying, and then thorough washing in water. Untreated fabrics did not retain any color after this treatment; however, all treated materials showed a pronounced color which ranged from light orange to dark brown, depending on the quaternary ammonium content. In one case (a sample identical to that of Sample #31), the fluorescein treated sample showed a weight gain of 27%. Further analysis on this sample for % nitrogen and % chloride was conducted by an independent laboratory (Galbraith Laboratories, Inc., Knoxville, Tenn.). The results (2.62% N and 6.83% Cl) indicate a slightly lower level than as calculated gravimetrically. This is likely due to the reasons described above. An exact control of % grafting is not a requirement of this invention. As described in the testing presented below, the antimicrobial activity of these materials is functional over a wide range of compositions.

The materials described by Sample #1 through Sample #40 are graft copolymers in which the quaternary ammonium polymeric grafts have a linear structure. These highly charged linear chains would be water-soluble if they were not tethered at one end to a cellulose substrate. Thus, the materials are capable of absorbing and holding water. Selected materials were tested for their ability to absorb and retain water. For instance, a 2.22 gram sample of the material of Sample #2 was found to retain 12.68 times its own weight of water when placed in a funnel and completely saturated. The samples prepared in Sample #41 and Sample #42 were found to retain water at 38 and 66 times their own weight, respectively. These two samples were prepared using a combination of monofunctional quaternary monomer, and a difunctional non-quaternary cross linking agent. The cross linking agent causes the grafted polymer chains to become branched, and also allows individual chains to form chemical bonds with each other that result in network formation. Once swollen with water, the polymer network becomes a slippery gel material. The absorbent biocidal materials produced with and without cross slinking agent have similar chemical and antimicrobial properties. Although the materials prepared using cross linking agents have extremely high absorbing capacity, they do tend to become rather slippery when wet.

This slippery property may be undesirable in some applications, particularly where this is the exposed surface. However, the two different variations may be utilized in conjunction with each other. For instance, the material of Sample #35 may be used as a shell or barrier material around the material of Sample #42. This would result in a bandage material having a superabsorbent compound interiorly to provide absorptive capacity, having inherent antimicrobial properties throughout, and having superior antimicrobial properties on the exterior (where a polymer having antimicrobial properties that are demonstrated superior to a polymer with superabsorptive capacity is employed in the outer location).

EXAMPLE 2

Testing of Antimicrobial Activity

All biological testing was performed by an independent testing laboratory (Biological Consulting Services of North Florida, Incorporated, Gainesville, Fla.). The first set of antimicrobial activity tests was performed using the absorbent antimicrobial material of Sample #21. The grafting yield for this sample was 26%. An untreated, unwashed sample of as-received sub#4 was used as a control. A sample of sub#1 treated with a siloxane based quaternary formulation (TMS, or 3-(trimethoxysilyl)-propyloctadecyldimethyl ammonium chloride) was also tested (sample #1122F). This sample contained approximately 9% quaternary siloxane which was applied from methanol solution. Based on a series of experiments with this quaternary siloxane, this is the maximum level which could be successfully applied to the substrate material. It was later found that the applied siloxane quaternary treatment was unstable, as evidenced by significant weight loss after washing the treated material after 30 days storage. This level is also higher than is typically achieved in antimicrobial treatments of similar substrates using commercial TMS products. It should also be noted that there were difficulties during the testing due to the hydrophobic (water-repellent) nature of the siloxane-treated material. Such properties are not desirable in a product designed specifically to be highly absorbent.

Gauze material from these three samples was aseptically cut into squares weighing 0.1+0.05 grams. This corresponds to a 1"×1" four-layer section. Each square was then individually placed in a sterile 15-mm petri dish and covered. One-milliliter tryptic soy broth suspension containing $10.^6$-cfu/ml mid-log phase $E.$ $coli$ (ATCC 15597) or $S.$ $aureus$ (ATCC 12600) was added to each gauze section. The plates were then incubated overnight at 37 C. Following incubation, the material was aseptically placed into 50-mL conical centrifuge tubes. Twenty-five milliliters of sterile phosphate buffered saline was then added to each tube. The tubes were shaken on a rotary shaker (Red Rotor PR70/75, Hoofer Scientific, CA) for 30 minutes. The eluant was then diluted accordingly and enumerated by aseptically spread plating onto Tryptic Soy Agar (TSA) plates. The plates were incubated overnight at 37 C. All gauze samples were processed in triplicates. The results of this testing are summarized in Table 2.

TABLE 2

Results of antimicrobial activity testing.

| | cfu/mL | |
|---|---|---|
| Sample | *Staphylococcus aureus* | *Escherichia coli* |
| Sub #4 (control) | $1.3 \times 10^6$ | $6.1 \times 10^6$ |
| | $4.6 \times 10^5$ | $2.4 \times 10^6$ |
| | $8.0 \times 10^5$ | $1.5 \times 10^6$ |
| Material of Sample #21 | <10 | <10 |
| | <10 | <10 |
| | <10 | <10 |
| TMS siloxane Material | <10 | $1.4 \times 10^4$ |
| | 20 | $2.3 \times 10^4$ |
| | 170 | $4.3 \times 10^4$ |

The results of this experiment are rather self-explanatory, and indicate that the material of Sample #21 was able to kill greater than 99.999% of both organisms. The siloxane-based quaternary ammonium sample (DC5700) was fairly effective on *S. aureus*, but only slightly effective on *E. coli*.

Further testing was carried out using the materials of Sample #9. A freshly-prepared sample of sub#1 treated with TMS siloxane quaternary ammonium (8%) was also tested, along with a washed untreated sub#1 control. In this experiment, freshly-prepared bacterial cultures containing additional TSB growth medium were used. The samples were treated as before. In addition, a second set of samples was reinoculated with additional bacterial culture after the first day of incubation, and allowed to incubate for an additional day. Data from these experiments is presented in Tables 3 and 4.

TABLE 3

Colony forming units (cfu) of 4 layer gauze strips cut into one inch² sections following inoculation with bacteria and overnight incubation.

| | cfu/mL | |
|---|---|---|
| Sample | *Staphylococcus aureus* | *Escherichia coli* |
| (Control) | $5.2 \times 10^7$ | $8.7 \times 10^7$ |
| (Sub #1 washed) | $2.1 \times 10^7$ | $4.6 \times 10^7$ |
| | $9.4 \times 10^7$ | $5.4 \times 10^7$ |
| TMS siloxane quat | $1.2 \times 10^6$ | $8.8 \times 10^6$ |
| (8% on Sub #1) | $9.1 \times 10^6$ | $1.3 \times 10^7$ |
| | $5.9 \times 10^6$ | $7.0 \times 10^6$ |
| Material of Sample #9 | $8.9 \times 10^1$ | $6.6 \times 10^1$ |
| (37% TMMC on Sub #1) | $3.7 \times 10^1$ | $3.6 \times 10^1$ |
| | $3.3 \times 10^1$ | $9.0 \times 10^0$ |

TABLE 4

Colony forming units (cfu) of 0.1-gram gauze strips following inoculation with the indicated bacteria, overnight incubation, re-inoculation, and overnight incubation.

| | cfu/mL | |
|---|---|---|
| Sample | *Staphylococcus aureus* | *Escherichia coli* |
| (Control) | $5.6 \times 10^8$ | $3.9 \times 10^8$ |
| (Sub #1 washed) | $2.6 \times 10^8$ | $3.8 \times 10^8$ |
| | $4.2 \times 10^8$ | $1.9 \times 10^8$ |

TABLE 4-continued

Colony forming units (cfu) of 0.1-gram gauze strips following inoculation with the indicated bacteria, overnight incubation, re-inoculation, and overnight incubation.

| | cfu/mL | |
|---|---|---|
| Sample | *Staphylococcus aureus* | *Escherichia coli* |
| TMS siloxane quat | $2.1 \times 10^6$ | $2.2 \times 10^8$ |
| (8% on Sub #1) | $1.8 \times 10^6$ | $1.8 \times 10^8$ |
| | $8.0 \times 10^5$ | $2.7 \times 10^8$ |
| Material of Sample #9 | $3.4 \times 10^1$ | $6.7 \times 10^2$ |
| (37% TMMC on Sub #1) | $3.8 \times 10^2$ | $7.2 \times 10^1$ |
| | $9.1 \times 10^1$ | $5.9 \times 10^1$ |

Again, the results of this experiment are self-explanatory. The siloxane-based quaternary ammonium did not show significant antibacterial activity, whereas the TMMC-grafted material did.

In another experiment, the antimicrobial effectiveness of several materials was tested in the presence of a high concentration of bodily fluids, as expected to occur in a heavily draining wound, for instance. The procedure was similar to that described above, except that the bacterial levels were higher ($10^8$ cfu/mL), and the inoculation mixture contained 50/50 newborn calf serum and TSB. The samples tested in this experiment were those of Samples #30 and 31. In addition, a sample of siloxane quaternary ammonium-treated knitted cotton material was obtained from a commercial supplier (Aegis). The results are presented in Table 5.

TABLE 5

Testing of biocidal absorbent materials in presence of 50% calf blood serum.

| | cfu/mL | |
|---|---|---|
| Sample | *Staphylococcus aureus* | *Escherichia coli* |
| Control | $5.9 \times 10^7$ | $2.7 \times 10^7$ |
| (Sub #5 J&J gauze) | $6.3 \times 10^7$ | $1.9 \times 10^7$ |
| | $7.1 \times 10^7$ | $9.8 \times 10^6$ |
| Siloxane quat on | $1.8 \times 10^7$ | $1.2 \times 10^6$ |
| Cotton fabric | $3.5 \times 10^7$ | $9.5 \times 10^5$ |
| | $1.5 \times 10^7$ | $7.0 \times 10^6$ |
| Material of Sample 30 | $1.0 \times 10^4$ | $<1.0 \times 10^0$ |
| (TMMC quat ~ 44% graft) | $1.2 \times 10^4$ | $5.0 \times 10^0$ |
| | $9.7 \times 10^3$ | $<1.0 \times 10^0$ |
| Material of Sample 31 | $2.4 \times 10^4$ | $3.9 \times 10^2$ |
| (TMMC quat ~ 48% graft) | $3.2 \times 10^4$ | $6.0 \times 10^0$ |
| | $1.2 \times 10^5$ | $1.0 \times 10^0$ |

As can be seen from the data in Table 5, the siloxane based quaternary treated material showed almost zero effectiveness. The TMMC-grafted material was extremely effective against e-coli, even in the presence of high concentrations of bodily fluids. The high serum protein concentration appeared to mask the effectiveness of the TMMC-grafted material to some extent; however, the levels of serum which were used in this experiment were quite challenging. Generally, in these types of experiments much lower serum levels are used (10 to 20%).

It is an aim of this invention to provide an absorbent antimicrobial material which does not leach or elute any soluble antimicrobial agent. In order to verify this, material of sample #31 (Table 1) was extraction tested under a range of pH conditions, and also in the presence of blood serum. In addition, a commercially available antimicrobial dressing was also tested under identical conditions. The commercially available antimicrobial dressing is "Kerlix-A.M.D. Antimicrobial Super Sponges", manufactured by Kendall Tyco Healthcare Group (active ingredient 0.2% Polyhexamethylene Biguanide) The following procedure was used: Approximately, a one square inch section of each bandage material was placed in a 50-mL sterile polypropylene tube. Twenty-five milliliters of phosphate buffered saline at pH 5.0, pH 7.0, pH 7.0 supplemented with 10% fetal bovine serum (FBS), or pH 9.0 was added to each tube. Each sample was processed in triplicates to assure reproducibility. pH values were adjusted using 0.1 N NaOH or HCl. The tubes ware then placed on a rotary shaker (Red Rotor PR70/75, Hoofer Scientific, CA) for and agitated mildly (40 rotations/min) for 16 hours. Tryptic Soy Agar (TSA) (Difco Laboratory, Detroit, Mich.) petri dishes were inoculated with a continuous lawn of either *E. coli* (ATCC 15597) or *S. aureus* (ATCC 12600) and the plates were divided into four sections. Twenty microliters of the soaked gauze aqueous extract was then placed onto the labeled sections of the bacteria inoculated plates. The plates were then covered and incubated at 37° C. for 18 hours. The plates were then visibly inspected for growth suppression at areas of inoculation. The results are presented in Table 6.

TABLE 6

Anti Microbial release test of supplied gauze material after soaking in Phosphate buffered saline (PBS) for 16 hours at various pH values.

| Sample | Effect of Gauze Extract on Bacterial Growth | |
|---|---|---|
| | *Staphylococcus aureus* | *Escherichia coli* |
| pH 5.0 | No Inhibition | No Inhibition |
| Material of Sample #31 | No Inhibition | No Inhibition |
| | No Inhibition | No Inhibition |
| pH 7.0 | No Inhibition | No Inhibition |
| Material of Sample #31 | No Inhibition | No Inhibition |
| | No Inhibition | No Inhibition |
| pH 7.0 | No Inhibition | No Inhibition |
| Material of Sample #31 with 10% FBS | No Inhibition | No Inhibition |
| | No Inhibition | No Inhibition |
| pH 9.0 | No Inhibition | No Inhibition |
| Material of Sample #31 | No Inhibition | No Inhibition |
| | No Inhibition | No Inhibition |
| pH 5.0 (Kerlix AMD) | Inhibition | No Inhibition |
| | Inhibition | No Inhibition |
| | Inhibition | No Inhibition |
| pH 7.0 (Kerlix AMD) | Inhibition | No Inhibition |
| | Inhibition | No Inhibition |
| | Inhibition | No Inhibition |
| pH 7.0 with 10% FBS (Kerlix AMD) | Inhibition | No Inhibition |
| | Inhibition | No Inhibition |
| | Inhibition | No Inhibition |
| pH 9.0 (Kerlix AMD) | Inhibition | No Inhibition |
| | Inhibition | No Inhibition |
| | Inhibition | No Inhibition |

As seen from the results listed in Table 6, the material of sample #31 did not leach or release any antimicrobial agent under any of the conditions tested; however, the commercial antimicrobial dressing, Kerlix AMD, was found to release antimicrobial agent toxic to s. aureus under all testing conditions. Such leaching of active agent may have an undesirable effect on wound healing, and also cause decreased antimicrobial effectiveness of the dressing. Further antimicrobial testing in the presence of 10% blood serum was performed using additional organisms as described below. These included a number of common pathogenic bacteria, as well as at least one fungal species. The material of Sample #32 was tested, and untreated sub#5 was used as a control. The gauze material was aseptically cut into approximately one inch square sections. Sub#5 gauze sample consisted of material in four layers and the material of Sample #32 consisted of two layers. Both types of samples weighed approximately 0.1 gram. Each sample section was individually placed in a sterile 100×15-mm petri dish and covered. *Escherichia coli* (ATCC 15597), *Staphylococcus aureus* (ATCC 12600), *Klebsiella pneumoniae* (ATCC 13883), *Pseudomonas aeruginosa* (ATCC 51447), *Proteus vulgaris* (ATCC 13115), *Serratia marcescens* (ATCC13880), *Enterococcus faecalis* (ATCC 19433), and *Enterobacter aerogenes* (ATCC 13048) were grown in twenty five milliliters of tryptic soy broth (TSB) (Difco Laboratory, Detroit, Mich.) for 16 hours at 37° C. Each bacterial culture was then diluted in Fresh TSB containing 10% Fetal Bovine Serum (Sigma, St. Louis, Mo.) to a final concentration of approximately $10.\text{sup}.5\text{-cfu/mL}$. One milliliter of each bacterial suspension was added to each gauze section. Each section was inoculated with only one bacterial species. All gauze samples were inoculated in triplicates. The petri dish containing the inoculated sample was then incubated for 18 hours at 37° C. in 95% humidity. Following incubation, the gauze material was aseptically placed into 50-mL conical centrifuge tubes. Twenty-five milliliters of sterile phosphate buffered saline (PBS) was then added to each tube. The tubes were shaken on a rotary shaker (Red Rotor PR70/75, Hoofer Scientific, CA) for 30 minutes. The eluant was then serially diluted. Tenfold dilutions were performed by the addition of 0.3-ML of sample to 2.7-mL of sterile PBS. Aliquots of each dilution or of the original undiluted sample were then aseptically spread plated onto Tryptic Soy Agar (TSA) (Difco Laboratory, Detroit, Mich.) plates. The plates were incubated for 18 hours at 37° C. The colonies on the respective plates were counted and concentrations were determined. The fungus *Candida albicans* was used in the same procedure outlined above, except incubation times were doubled and Sabouraud Dextrose Broth and agar (Difco Laboratory, Detroit, Mich.) were used instead of TSB and TSA, respectively. The results are summarized in Table 7. The reported bacterial levels are diluted by a factor of 25× versus the level present in the actual gauze samples.

TABLE 7

Antimicrobial activity results for various organisms.

| | Sample | |
|---|---|---|
| Organism | Sub 5* (control) | Material of sample 32 |
| *S. aureus* | $5.9 \times 10^6$ | $<2.0 \times 10^0$ |
| *S. aureus* | $6.3 \times 10^7$ | $<2.0 \times 10^0$ |
| *S. aureus* | $7.1 \times 10^7$ | $<2.0 \times 10^0$ |
| *E. coli* | $1.7 \times 10^6$ | $<2.0 \times 10^0$ |
| *E. coli* | $1.9 \times 10^6$ | $<2.0 \times 10^0$ |
| *E. coli* | $2.4 \times 10^6$ | $<2.0 \times 10^0$ |
| *K. pneumoniae* | $1.8 \times 10^6$ | $<2.0 \times 10^0$ |
| *K. pneumoniae* | $1.4 \times 10^6$ | $<2.0 \times 10^0$ |
| *K. pneumoniae* | $3.7 \times 10^6$ | $<2.0 \times 10^0$ |
| *P. aeruginosa* | $2.1 \times 10^7$ | $<2.0 \times 10^0$ |
| *P. aeruginosa* | $3.9 \times 10^7$ | $<2.0 \times 10^0$ |
| *P. aeruginosa* | $4.3 \times 10^7$ | $<2.0 \times 10^0$ |
| *P. vulgaris* | $2.8 \times 10^6$ | $<2.0 \times 10^0$ |
| *P. vulgaris* | $1.1 \times 10^7$ | $<2.0 \times 10^0$ |
| *P. vulgaris* | $3.7 \times 10^6$ | $<2.0 \times 10^0$ |
| *S. marcescens* | $6.7 \times 10^7$ | $<2.0 \times 10^0$ |
| *S. marcescens* | $7.3 \times 10^7$ | $<2.0 \times 10^0$ |
| *S. marcescens* | $8.7 \times 10^7$ | $<2.0 \times 10^0$ |
| *E. faecalis* | $3.8 \times 10^6$ | $<2.0 \times 10^0$ |
| *E. faecalis* | $1.7 \times 10^6$ | $<2.0 \times 10^0$ |
| *E. faecalis* | $2.9 \times 10^6$ | $<2.0 \times 10^0$ |
| *E. aerogenes* | $1.1 \times 10^7$ | $<2.0 \times 10^0$ |
| *E. aerogenes* | $3.3 \times 10^7$ | $<2.0 \times 10^0$ |
| *E. aerogenes* | $2.9 \times 10^7$ | $<2.0 \times 10^0$ |

TABLE 7-continued

Antimicrobial activity results for various organisms.

| | Sample | |
|---|---|---|
| Organism | Sub 5* (control) | Material of sample 32 |
| C. albicans | $5.9 \times 10^5$ | $2.0 \times 10^0$ |
| C. albicans | $7.2 \times 10^5$ | $4.0 \times 10^0$ |
| C. albicans | $1.2 \times 10^6$ | $5.0 \times 10^0$ |

*values represent cfu/mL of the 25-mL PBS solution used to elute the microorganisms from the gauze sections.

The results presented in Table 7 indicate significant antimicrobial activity for the TMMC-grafted material against a variety of organisms. Further testing of this material was conducted using several bacteriophages. Bacteriophages are viral organisms which infect a particular bacterial host. In this method, the antimicrobial material is inoculated with the viral agent and then allowed to incubate for a specified period. The amount of viable viral organism is then determined on the basis of remaining ability to infect the host bacteria. Samples were aseptically cut into approximately one inch.sup.2 square sections. Sub#5 gauze sample consisted of material in four layers and the material of Sample #32 consisted of material in two layers. Each sample weighed approximately 0.1 g. Each sample section was individually placed in a sterile 100×15-mm petri dish and covered. Stocks of the following bacteriophages, MS2 (ATCC 15597-B1), .phi.X-174 (ATCC 13706-B1), and PRD-1 were added to 10 mL of TSB containing 10% Fetal Bovine Serum (Sigma, St. Louis, Mo.) to a final concentration of approximately 10.sup.6-cfu/mL. One milliliter of each bacterial suspension was added to each gauze section. All gauze samples were inoculated in triplicates. The petri dish containing the inoculated sample was then incubated for 18 hours at 37° C. in 100% humidity. Following incubation, the gauze material was aseptically placed into 50-mL conical centrifuge tubes. Twenty-five milliliters of sterile phosphate buffered saline (PBS) was then added to each tube. The tubes were shaken on a rotary shaker (Red Rotor PR70/75, Hoofer Scientific, CA) for 30 minutes. The eluant was then serially diluted. Tenfold dilutions were performed by the addition of 0.3-ML of sample to 2.7-mL of sterile PBS. Phages were assayed as plaque-forming units (pfu) using their respective hosts (MS2 (ATCC 15597-B1), *Escherichia coli* C-3000 (ATCC 15597); .phi.X-174 (ATCC 13706-B1), *E. coli* (ATCC 13706); and PRD-1, *Salmonella typhimurium* (ATCC 19585)). The soft-agar overlay method (Snustad, S. A. and D. S. Dean, 1971, "Genetic Experiments with Bacterial Viruses". W.H. Freeman and Co., San Francisco) was used for enumerating the phages. The results are presented in Table 8.

TABLE 8

Testing of absorbent antimicrobial materials against viral agents.

| | Sample | |
|---|---|---|
| Bacteriophage | Sub #5 (control)* | Material of sample 32 |
| MS-2 | $3.3 \times 10^4$ | $<2.0 \times 10^0$ |
| MS-2 | $4.1 \times 10^4$ | $<2.0 \times 10^0$ |
| MS-2 | $2.3 \times 10^4$ | $<2.0 \times 10^0$ |
| PRD1 | $1.7 \times 10^5$ | $1.2 \times 10^2$ |
| PRD1 | $7.9 \times 10^4$ | $1.5 \times 10^2$ |
| PRD1 | $8.8 \times 10^4$ | $1.7 \times 10^2$ |
| φX-174 | $8.7 \times 10^3$ | $2.4 \times 10^3$ |

TABLE 8-continued

Testing of absorbent antimicrobial materials against viral agents.

| | Sample | |
|---|---|---|
| Bacteriophage | Sub #5 (control)* | Material of sample 32 |
| φX-174 | $1.2 \times 10^4$ | $1.1 \times 10^3$ |
| φX-174 | $9.0 \times 10^3$ | $1.7 \times 10^3$ |

*values represent pfu/mL of the 25-mL PBS solution used to elute the microorganisms from the gauze sections.

As seen from the results in Table 8, the absorbent antimicrobial material has significant effectiveness against viral pathogens, as evidenced by reduction or loss of bacteriophage activity in the treated sample #32. These results, in combination with the results regarding bacterial and fungal organisms, indicate a relatively broad antimicrobial potential for compositions of the invention.

In additional testing, several absorbent antimicrobial dressing materials not based on acrylate materials were studied. These tests included the materials of Samples #33, with VBTAC, and #34, with DADMAC. The material was aseptically cut into two layer square sections of approximately one inch.sup.2. Each square was individually placed in a sterile 100×15-mm petri dish and covered. *E. coli* (ATCC 15597) and *S. aureus* (ATCC 12600) were grown in twenty five milliliters of tryptic soy broth (TSB) (Difco Laboratory, Detroit, Mich.) for 16 hours at 37° C. Each bacterial culture was then diluted in Fresh TSB containing 10% Fetal Bovine Serum (Sigma, St. Louis, Mo.) to a final concentration of approximately 10.sup.5-cfu/mL. One milliliter of each bacterial suspension was added to each gauze section. Each section was inoculated with only one bacterial species. All gauze samples were inoculated in triplicates. The petri dish containing the inoculated sample was then incubated for 16 hours at 37° C. in 95% humidity. Following incubation, the gauze material was aseptically placed into 50-mL conical centrifuge tubes. Twenty-five milliliters of sterile phosphate buffered saline (PBS) was then added to each tube. The tubes were shaken on a rotary shaker (Red Rotor PR70/75, Hoofer Scientific, CA) for 30 minutes. The eluant was then serially diluted. Tenfold dilutions were performed by the addition of 0.3-ML of sample to 2.7-mL of sterile PBS. Aliquots of each dilution or of the original undiluted sample were then aseptically spread plated onto Tryptic Soy Agar (TSA) (Difco Laboratory, Detroit, Mich.) plates. The plates were incubated for 18 hours at 37° C. The colonies on the respective plates were counted and concentrations were determined. The results are summarized in Table 9.

TABLE 9

Colony forming units (cfu) present in the PBS eluant (25-mL) of the indicated gauze sections (1-inch2) following their inoculation with bacteria and overnight incubation.

| | cfu/mL of the PBS eluant | |
|---|---|---|
| Sample | *Staphylococcus aureus* | *Escherichia coli* |
| SUB 5 (CONTROL) | $7.6 \times 10^6$ | $1.6 \times 10^8$ |
| | $6.9 \times 10^6$ | $2.9 \times 10^8$ |
| | $5.8 \times 10^6$ | $1.3 \times 10^8$ |
| Material of Sample #33 15% VBTAC graft | $<1.0 \times 10^0$ | $<1.0 \times 10^0$ |
| | $<1.0 \times 10^0$ | $<1.0 \times 10^0$ |
| | $<1.0 \times 10^0$ | $<1.0 \times 10^0$ |
| Material of Sample #34 7% DADMAC graft | $3.0 \times 10^0$ | $<1.0 \times 10^0$ |
| | $4.0 \times 10^0$ | $<1.0 \times 10^0$ |
| | $<1.0 \times 10^0$ | $<1.0 \times 10^0$ |

As shown in the table, the material with grafted quaternary ammonium polymer showed significant antimicrobial activity, even in the presence of 10% blood serum.

Additional verification of the nonleaching nature of the subject materials was obtained by Kirby-Bauer zone of inhibition tests. Sample #32 was used in this experiment, along with a control of substrate #5. The following procedure was used: Material was aseptically cut into: 0.5×0.5 cm square sections, 0.2×2.0 cm strips, and 1.0×6.0 strips. All material was used in one-layer sections. *Escherichia coli* (ATCC 15597), and *Staphylococcus aureus* (ATCC 12600) were grown in five milliliters of tryptic soy broth (TSB) (Difco Laboratory, Detroit, Mich.) for 5 hours at 37° C. 0.5-mL of either bacterial culture was then added to molten (45° C.) sterile Tryptic Soy Agar (TSA) (Difco Laboratory, Detroit, Mich.). The mixture was then swirled and poured into a 15×100-mm petri dish. The gauze material was then aseptically placed onto the surface of the agar and the agar was allowed to solidify. The petri dish containing the sample was then incubated for 18 hours at 37° C. in 95% humidity. Zones of bacterial growth inhibition were then measured. Results are shown in Table 10.

TABLE 10

Results of zone of inhibition testing of Sample #32.

| Sample/section size | Zone of inhibition around sample (mm) | |
| --- | --- | --- |
| | S. aureus | E. coli |
| SUB 5/1.5 × 1.5 | <0.1 | <0.1 |
| SUB 5/2.0 × 2.0 | <0.1 | <0.1 |
| SUB 5/1.0 × 5.0 | <0.1 | <0.1 |
| Sample #32/1.5 × 1.5 | <0.1 | <0.1 |
| Sample #32/2.0 × 2.0 | <0.1 | <0.1 |
| Sample #32/1.0 × 5.0 | <0.1 | <0.1 |

As shown in Table 10, no measurable zone of inhibition was observed around either the control or treated samples.

A study was conducted to determine the speed of antimicrobial action for the subject materials. Material similar in composition to sample #33 (code #0712A) was used in this study, along with an untreated control (substrate #5). The following procedure was employed. Material was aseptically cut into approximately one inch square sections. 0712A gauze sample consisted of material in two layers, and SUB-5 samples were in 3 layers. Each sample section was individually placed in a sterile 100×15-mm petri dish and covered. *Staphylococcus aureus* (ATCC 12600) was grown in twenty-five milliliters of tryptic soy broth (TSB) (Difco Laboratory, Detroit, Mich.) for 6 hours at 37 C. The bacterial culture was then diluted in Fresh 1% TSB containing 10% Fetal Bovine Serum (Sigma, St. Louis, Mo.) to a final concentration of approximately $10^6$-cfu/mL. One half (0.5) milliliter of the bacterial suspension was added to each gauze section. All gauze samples were inoculated in duplicates. The petri dish containing the inoculated sample was then incubated for the indicated time points at 37° C. in 95% humidity. Following incubation, the gauze material was aseptically placed into 50-mL conical centrifuge tubes. Twenty-five milliliters of sterile phosphate buffered saline (PBS) was then added to each tube. The tubes were shaken on a rotary shaker (Red Rotor PR70/75, Hoofer Scientific, CA) for 10 minutes. The eluant was then serially diluted. Tenfold dilutions were performed by the addition of 0.3-ML of sample to 2.7-mL of sterile PBS. Aliquots of each dilution or of the original undiluted sample were then aseptically spread plated in duplicates onto Tryptic Soy Agar (TSA) (Difco Laboratory, Detroit, Mich.) plates. The plates were incubated for 18 hours at 37° C. The colonies on the respective plates were counted and concentrations were determined. Results of this rate study are presented in Table 11.

TABLE 11

Effect of 0712A and Sub 5 gauze material on the inactivation of *Staphylococcus aureus* at different exposure times.

| | Sample (and respective bacterial count at specified times) | |
| --- | --- | --- |
| Time | Sub 5 | 0712A |
| 1 minute | $1.5 \times 10^5$ | $3.0 \times 10^2$ |
| | $1.9 \times 10^5$ | $3.1 \times 10^2$ |
| 10 minutes | $1.3 \times 10^5$ | $2.0 \times 10^2$ |
| | $2.5 \times 10^5$ | $8.0 \times 10^1$ |
| 20 minutes | $1.5 \times 10^5$ | $8.0 \times 10^1$ |
| | $2.3 \times 10^5$ | $1.2 \times 10^2$ |
| 30 minutes | $1.6 \times 10^5$ | $1.1 \times 10^1$ |
| | $2.8 \times 10^5$ | $2.1 \times 10^1$ |
| 60 minutes | $1.9 \times 10^5$ | $1.2 \times 10^1$ |
| | $2.1 \times 10^5$ | $1.9 \times 10^1$ |
| 4 hours | $3.3 \times 10^5$ | $3 \times 10^0$ |
| | $2.5 \times 10^5$ | $1.2 \times 10^1$ |
| 8 hours | $4.0 \times 10^6$ | $<2.0 \times 10^0$ |
| | $4.8 \times 10^6$ | $4.0 \times 10^0$ |
| 12 hours | $2.3 \times 10^7$ | $6.0 \times 10^0$ |

[1] values represent cfu/Ml of the 25-mL PBS solution used to elute the microorganisms from the gauze sections.

The data clearly indicates that significant antimicrobial activity is manifested very quickly. Approximately 99.8% of *S. aureus* is destroyed in as little as one minute.

Samples similar in composition to that of sample #31 in Table 1 were subjected to sterilization by several methods including: autoclaving, ethylene oxide exposure, gamma irradiation (2.5 Mrad), and electron beam irradiation (2.5 Mrad). No observable degradation of physical properties or loss of antimicrobial activity was observed.

Samples #43, #44 and #45 (see Table 1) were reacted for significantly shorter periods of time than the other samples listed; however, relatively high grafting yields were still obtained. This demonstrates that the process can be achieved quickly, which will have economic advantages for large-scale industrial application of this invention. It is likely that sufficiently high grafting yields can be obtained in 5 minutes or less under appropriate conditions.

Thus, the present invention teaches and demonstrates the effectiveness of a composition comprised of a substrate, preferably fibrous and water-insoluble, to which are attached by non-hydrolyzing covalent bonds a multitude of polymeric chains bearing quaternary ammonium groups. These chains predominantly contain more than one quaternary ammonium group per chain, and preferably have varying lengths and extend varying distances (measured at the molecular level) from the substrate. The present invention also teaches the manufacture of such compositions, where the preferred manufacture includes the steps of dewatering and drying the composition so it is available in a dry (not a hydrogel) form that is more capable of taking up wound exudate.

The present data demonstrates the superior effectiveness of compositions of the present invention compared with siloxane-based polymers such as taught by Blank et al. in U.S. Pat. No. 5,045,322. The '322 patent teaches attachment of monomeric siloxane-based quaternary compounds to super absorptive polymers. The siloxane-based compounds are sensitive to hydrolysis, as noted in the parent application. These siloxane compounds are expected to be more easily hydrolyzed than the acrylate polymers used in the present application.

Furthermore, other polymers used in the present invention (such as those based on DADMAC or trialkyl(p-vinylbenzyl) ammonium chloride) are substantially more stable to hydrolysis than the bonds taught in the '322 patent.

In the case of siloxane-based antimicrobial agents, the chemical bonds which are susceptible towards hydrolysis are part of the backbone structure of the polymer. Hydrolysis of even a single siloxane linkage can result in the cleavage of several quaternary units (although the siloxane polymers in such systems are generally only a few units in length). In contrast, in the case of grafted acrylate polymers of the present invention, the grafted chains may be hundreds of units long. The ester linkages which attach the quaternary groups to the polymer backbone are inherently more stable than the linkages in the bulky siloxane quaternary units. Even so, it is possible that the acrylates can be hydrolyzed under extreme conditions. However, since the hydrolyzable group of the acrylate is not in the main chain of the polymer, this will not result in chain cleavage, so the loss under such unlikely, extreme conditions would be limited to a single quaternary unit per hydrolysis event.

Further, the antimicrobial effectiveness of a bulky molecule like the TMS siloxane used by Blank et al. is reduced somewhat by its steric hindrance. Since it can and does fold on itself, the number of such molecules that can be bonded to a given surface is limited as compared to smaller molecules. Further, the fact that the nitrogen atom can be blocked by other atoms in the molecule limits its positive charge density as well. The consequence of this is that the antimicrobial is less effective than one that can be attached to the same surface in greater numbers or density per unit area. Since the net positive charge on the nitrogen atom is related to the effectiveness of the antimicrobial, one that has more exposed positive atoms would theoretically be more effective. This can be shown by comparing the effectiveness of the Blank et al. compounds to any other quaternary compounds that have less steric hindrance. This is demonstrated in the results above, in Tables 2-5. Another consequence is that in the presence of proteinaceous matter such as blood, urine, and tissue cells, the '322 compounds can be blocked more easily than quaternary polymers having a greater concentration of unhindered net positive charges. (See the parent application, PCT/US99/29091, and Table 5.)

A further shortcoming of the siloxane quaternary material disclosed according to Blank et al. is that it only provides a monolayer coverage of the surface. That is, the siloxane backbone molecules are not long-chain polymers. It is well known that siloxane chains more than a few units in length are particularly susceptible to hydrolysis, particularly those with bulky substituents such as the TMS monomer utilized in the '322 patent. This hydrolysis results in chain cleavage and loss of soluble antimicrobial. Such reactions occur as a result of cyclization or "back-biting" reactions (see: J. Semlyen, "Cyclic Polymers" Chapter 3, Elsevier, N.Y., 1986). By contrast, the surface according to the present invention is covered with polymeric chains composed of non-hydrolyzable carbon-carbon bonds, to which are bonded quaternary materials. Polymeric antimicrobials used according to the present invention are more effective than the monomeric antimicrobials described by Blank et al. (see Chen, Z. C., et al., "Quaternary Ammonium Functionalized Poly(propylene imine) Dendrimers as Effective Antimicrobials: Structure-Activity Studies", Biomacromolecules 1, p 473-480 (2000); Ikeda, T., "Antibacterial Activity of Polycationic Biocides", Chapter 42, page 743 in: High Performance Biomaterials, M. Szycher, ed., Technomic, Lancaster Pa., (1991); Donaruma, L. G., et al., "Anionic Polymeric Drugs", John Wiley & Son, New York, (1978)). Thus, in order to obtain a high antimicrobial activity, a high surface area base material must be used with the siloxane quaternary materials. The Blank et al. patent describes placing this monolayer antimicrobial treatment onto powders, which are then used to make superabsorbent polymer gels. The powder has a very high surface area, and hence the gels contain a lot of antimicrobial. However, the Blank et al. gels have almost zero mechanical strength, (and must be contained inside some type of matrix in order to form a useable device). In contrast, the modified cellulose fibers of the present invention have inherent mechanical properties which allow them to be directly used as structural devices such as bandages.

A common understanding in the art is that an "enhanced surface area" would not apply to monolayer treatments such as the siloxane system described by Blank et al. That is, an enhanced surface area substrate is needed to achieve high quaternary content. According to the present invention, however, a high quaternary content may be achieved even on low surface area fibers such as cotton because the quaternary materials of the present invention are polymeric. An analogy may be made to the "fuzzy" structure of a pipe-cleaner to describe a single substrate fiber modified by the currently-described method—that is, each "hair" of the pipe cleaner represents a polymer chain which has an antimicrobial group on substantially each monomer that makes up the polymer. The present applicants have actually attempted use of a Dow Corning product (TMS—the same compound described by Blank et al.) to treat fabrics, and have found that a significantly lower amount of quaternary antimicrobial groups could be applied. The bactericidal activity of the TMC treated fabrics was several orders of magnitude lower than the fabrics treated with polymeric quaternary materials. The inventors further found that the TMC-treated samples became water-repellent. This effect was reported by Blank et al. (see U.S. Pat. No. 5,035,892; column 12, line 57). This impairment of absorbency is undesirable in a product intended for use as an absorbent. Furthermore, the siloxane monomer has a higher MW than the monomers of the present invention. As a result, the effective quaternary material content (number of positively-charged sites per gram of material) is further reduced as compared to that of the present invention. Finally, the present application further discloses use of neutral or negatively charged antimicrobial polymers, which is neither disclosed nor suggested according to Blank et al.

It should also be noted that the mechanism of action of quaternary compounds is directed towards the cell membrane of the target organism. This process has been described as a mechanical "stabbing" (on a molecular level) which causes rupture of the cell membrane. Thus, it is not possible for pathogenic organisms to develop resistance as observed for most antibiotics.

Having generally described this invention, including the best mode thereof, those skilled in the art will appreciate that the present invention contemplates the embodiments of this invention as defined in the following claims, and equivalents thereof. However, those skilled in the art will appreciate that the scope of this invention should be measured by the claims appended hereto, and not merely by the specific embodiments exemplified herein. Those skilled in the art will also appreciate that more sophisticated technological advances will likely appear subsequent to the filing of this document with the Patent Office. To the extent that these later developed improvements embody the operative principles at the heart of the present disclosure, those improvements are likewise considered to come within the ambit of the following claims.

What is claimed is:

1. An antimicrobial bandage material comprising;
   a. a first substrate;
   b. an antimicrobial superabsorbent polymer, wherein said superabsorbent polymer is non-leachably bound to said first substrate, and wherein said superabsorbent polymer imparts antimicrobial activity to the bound said first substrate;
   c. a second substrate;
   d. a non-superabsorbent polymer, wherein said non-superabsorbent polymer is non-leachably bound to said second substrate, and wherein said non-superabsorbent polymer imparts antimicrobial activity to the bound said second substrate;
   wherein said second substrate and bound non-superabsorbent polymer covers or surrounds said first substrate and bound superabsorbent polymer,
   wherein said superabsorbent polymer consists essentially of polymers of a first monomeric quaternary ammonium salt and at least one cross linking agent,
   wherein said non-superabsorbent polymer consists essentially of polymers of a second monomeric quaternary ammonium salt, and
   wherein said first monomeric quaternary ammonium salt and second monomeric quaternary ammonium salt are selected, independently, from the group consisting of [2-(methacryloxloxy)ethyl]trimethylammonium chloride, also known as TMMC, [2-(acryloyloxy)ethyl]trimethylammonium methyl sulfate, also known as TMAS, [2-(acryloyloxy)ethyl)trimethylammonium chloride, also known as TMAC, [3-(methacryloylamino) propyl]trimethylammonium chloride, also known as TMAPMC, vinylbenzyltrimethylammonium chloride, also known as VBTAC, and diallyldialkylammonium salts.

2. The antimicrobial bandage material of claim 1, wherein said cross linking agent is an acrylate cross linking agent.

3. The antimicrobial bandage material of claim 1, wherein said cross linking agent is poly(ethylene glycol)diacrylate.

4. The antimicrobial bandage material of claim 1, wherein said first monomeric quaternary ammonium salt is selected from the group consisting of VBTAC and diallyldialkylammonium salts.

5. The antimicrobial bandage material of claim 4, wherein said first monomeric quaternary ammonium salt is a diallyldialkylammonium salt.

6. The antimicrobial bandage material of claim 5, wherein said first monomeric quaternary ammonium salt is diallyldimethylammonium chloride, also known as DADMAC.

7. The antimicrobial bandage material of claim 1, wherein said second monomeric quaternary ammonium salt is selected from the group consisting of VBTAC and diallyldialkylammonium salts.

8. The antimicrobial bandage material of claim 7, wherein said second monomeric quaternary ammonium salt is a diallyldialkylammonium salt.

9. The antimicrobial bandage material of claim 8, wherein said second monomeric quaternary ammonium salt is diallyldimethylammonium chloride, also known as DADMAC.

10. The antimicrobial bandage material of claim 1, wherein either or both of said first substrate and said second substrate are comprised, in whole or in part, of cellulose, or other naturally-derived polymers.

11. The antimicrobial bandage material of claim 1, wherein either or both of said first substrate and said second substrate are comprised, in whole or in part, of a synthetic polymer.

12. The antimicrobial bandage material of claim 11, wherein said synthetic polymer is polyethylene, polypropylene, nylon, polyester, polyurethane, or silicone.

13. The antimicrobial bandage material of claim 1, wherein said antimicrobial bandage material comprises all or part of a wound dressing, an intrinsically antimicrobial absorbent dressing, a burn dressing, or a gauze roll.

14. The antimicrobial bandage material of claim 1, wherein either or both of said first substrate and said second substrate is a woven or nonwoven flexible matrix, and wherein said antimicrobial bandage material is formed into the shape of a wound dressing, an intrinsically antimicrobial absorbent dressing, a burn dressing, or a gauze roll.

15. The antimicrobial bandage material of claim 5, wherein either or both of said first substrate and said second substrate is a woven or nonwoven flexible matrix, and wherein said antimicrobial bandage material is formed into the shape of a wound dressing, an intrinsically antimicrobial absorbent dressing, a burn dressing, or a gauze roll.

16. The antimicrobial bandage material of claim 6, wherein either or both of said first substrate and said second substrate is a woven or nonwoven flexible matrix, and wherein said antimicrobial bandage material is formed into the shape of a wound dressing, an intrinsically antimicrobial absorbent dressing, a burn dressing, or a gauze roll.

17. The antimicrobial bandage material of claim 8, wherein either or both of said first substrate and said second substrate is a woven or nonwoven flexible matrix, and wherein said antimicrobial bandage material is formed into the shape of a wound dressing, an intrinsically antimicrobial absorbent dressing, a burn dressing, or a gauze roll.

18. The antimicrobial bandage material of claim 9, wherein either or both of said first substrate and said second substrate is a woven or nonwoven flexible matrix, and wherein said antimicrobial bandage material is formed into the shape of a wound dressing, an intrinsically antimicrobial absorbent dressing, a burn dressing, or a gauze roll.

19. The antimicrobial bandage material of claim 1, further comprising a hemostatic agent.

20. The antimicrobial bandage material of claim 1, further comprising an indicator.

* * * * *